United States Patent
Cho et al.

(10) Patent No.: US 10,155,024 B2
(45) Date of Patent: Dec. 18, 2018

(54) COMPOSITION FOR PREVENTING OR TREATING B-CELL LYMPHOMA COMPRISING IL-21 EXPRESSING MESENCHYMAL STEM CELLS

(71) Applicant: THE CATHOLIC UNIVERSITY OF KOREA INDUSTRY-ACADEMIC COOPERATION FOUNDATION, Seoul (KR)

(72) Inventors: Seok Goo Cho, Seoul (KR); Nayoun Kim, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/671,626

(22) Filed: Mar. 27, 2015

(65) Prior Publication Data
US 2016/0008435 A1     Jan. 14, 2016

(30) Foreign Application Priority Data

Mar. 28, 2014 (KR) .......... 10-2014-0037219
Mar. 27, 2015 (KR) .......... 10-2015-0043338

(51) Int. Cl.
*A61K 48/00* (2006.01)
*A61K 38/20* (2006.01)
*A61K 35/28* (2015.01)

(52) U.S. Cl.
CPC .............. *A61K 38/20* (2013.01); *A61K 35/28* (2013.01)

(58) Field of Classification Search
None
See application file for complete search history.

(56) References Cited

U.S. PATENT DOCUMENTS

2015/0044134 A1* 2/2015 Lossos .......... A61K 45/06
                                                        424/1.11

FOREIGN PATENT DOCUMENTS

| KR | 2002-0091170 | 12/2002 |
| KR | 2008-0039844 | 12/2007 |
| KR | 2012-0133389 | 11/2014 |
| WO | WO 2013/109904 A1 | 7/2013 |

OTHER PUBLICATIONS

Kim et al (The Journal of Cell therapy, Apr. 2014. vol. 16, Issue 4, Supplement, p. S35).*
Zhang et al (Journal of Ovarian Research, 2014, vol. 7, No. 8, pp. 1-10).*
Chen et al (Molecular Therapy, 2008. vol. 16, No. 4, pp. 749-756).*
Li et al (Stem Cell Investigation, 2015, vol. 2:6, 1-5).*
Dwyer et al (Stem Cell Research & Therapy 2010, vol. 1: 25, pp. 1-7).*
Li et al (RSC Advances, 2016, vol. 6, pp. 36910-36922).*
Hu et al.(Biotechnology and Applied Biochemistry, 2011, vol. 58, No. 6, pp. 397-404).*
Roda et al (The Journal of Immunology, 2006. vol. 177, pp. 120-129).*
Korean Office Action for KR-10-2015-0043338, dated Jun. 15, 2016 without an English Translation, 5 pages.
Zhang et al. "Gene therapy of ovarian cancer using IL-21-secreting human umbilical cord mesenchymal stem cells in nude mice", Journal of Ovarian Research 2014, vol. 7(8): 1-10.

* cited by examiner

*Primary Examiner* — Celine X Qian
(74) *Attorney, Agent, or Firm* — Leydig, Voit & Mayer, Ltd.

(57) ABSTRACT

Provided is a pharmaceutical composition for preventing or treating B-cell lymphoma including IL-21 expressing mesenchymal stem cells, and a treating method using the same.

5 Claims, 5 Drawing Sheets

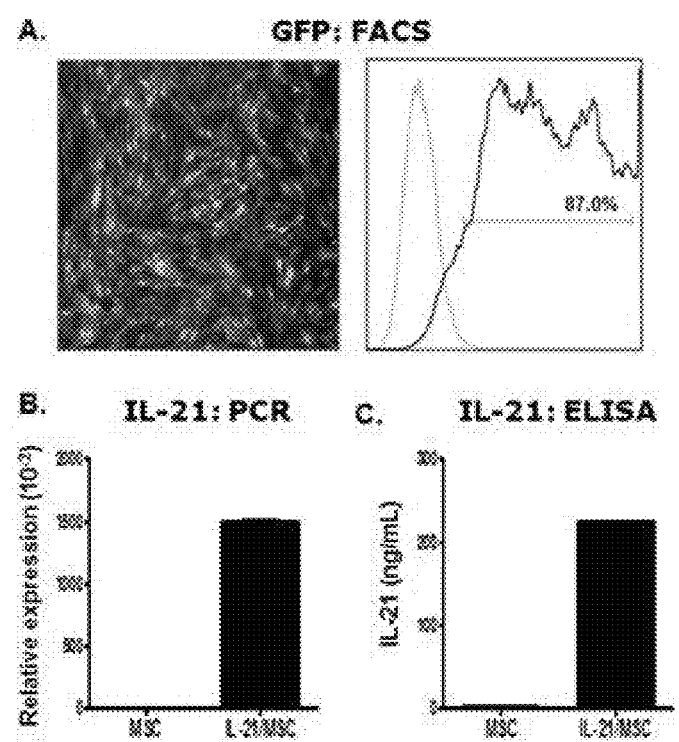

[FIG. 2]
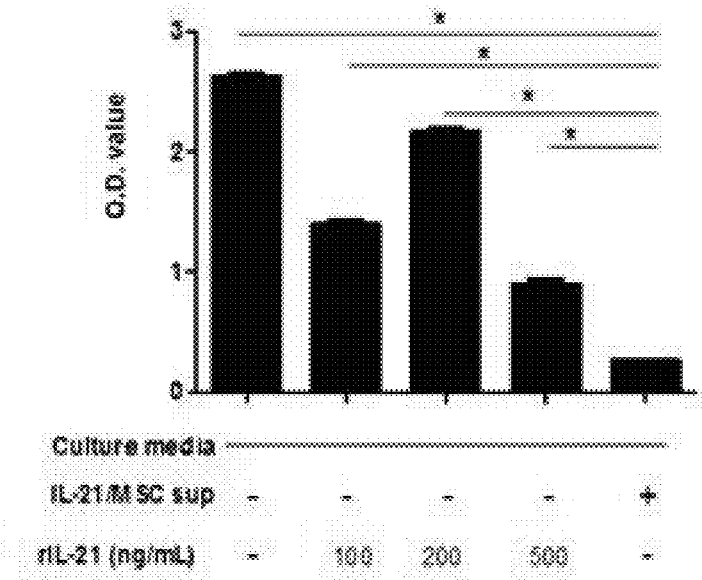
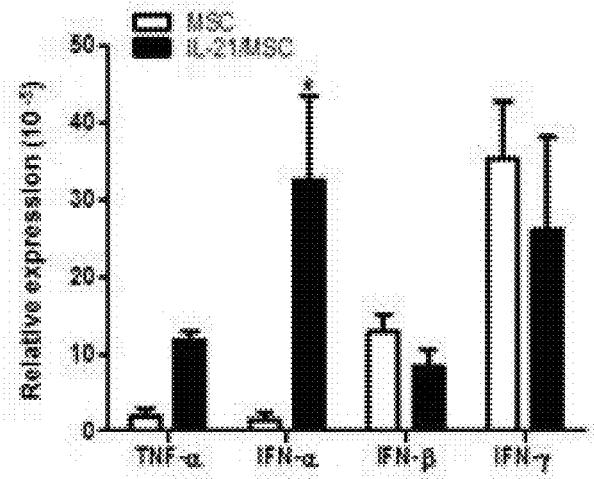

[FIG. 3]
A.
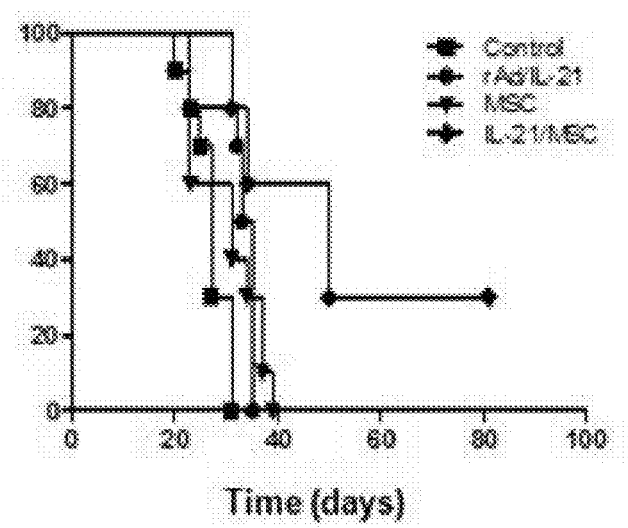
B.
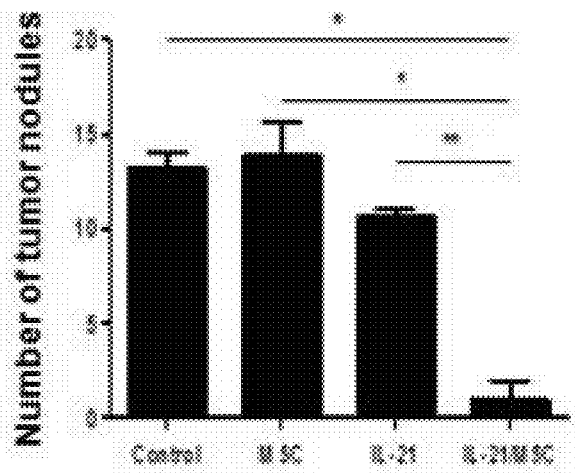

[FIG. 4]
A. IL-21 expressed in liver (ELISA)
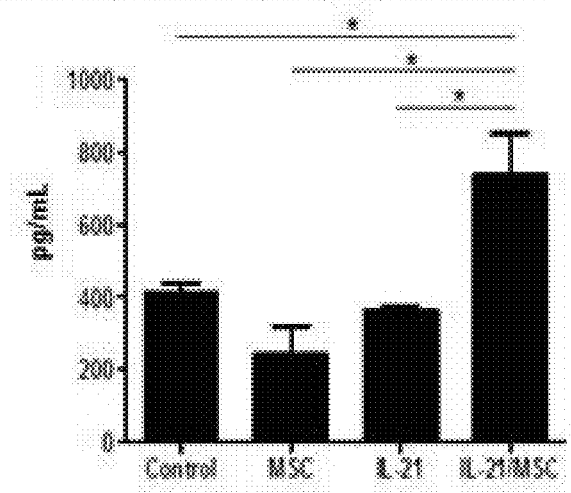
B. IL-21 expressed in spleen (RT-PCR)
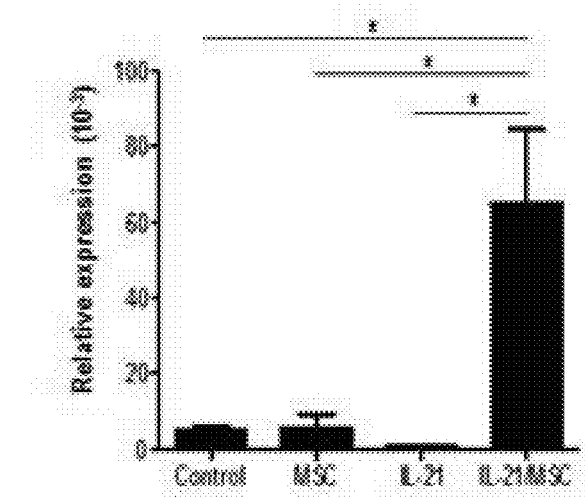

[FIG. 5]
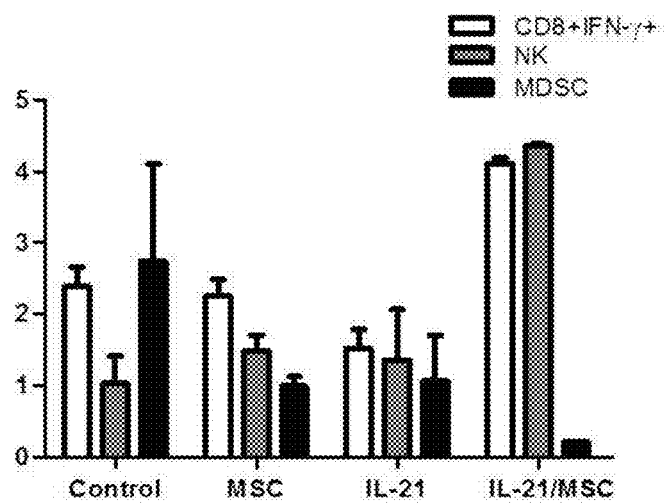
[FIG. 6]
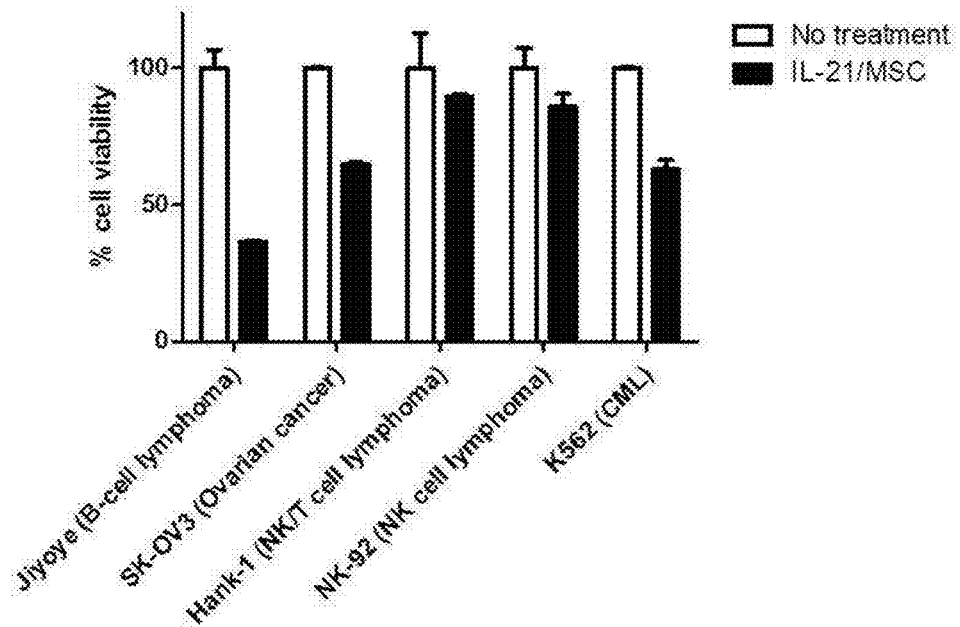

COMPOSITION FOR PREVENTING OR TREATING B-CELL LYMPHOMA COMPRISING IL-21 EXPRESSING MESENCHYMAL STEM CELLS

BACKGROUND

1. Field of the Invention

The present invention relates to a pharmaceutical composition for preventing or treating B-cell lymphoma including IL-21 (Interleukin-21) expressing mesenchymal stem cells, and a treating method using the same.

2. Discussion of Related Art

B cells express antibodies that each specifically response to various antigens, and thus, there are all kinds of B cells. The diversity of the B cells is important for an immune system. For human, each of the B cells can produce many antibody molecules. When a foreign antigen is neutralized, the production of the antibody is almost reduced, substantially. However, in some cases, proliferation of a certain B cells is sustained, and a tumor that is called "B cell lymphoma" may occur due to such a proliferation.

A typical tumor that characterizes the malignant growth of a B lymphocyte is non-Hodgkin's lymphoma (NHL). According to American Cancer Society, 65% of the patients diagnosed with the non-Hodgkin's lymphoma are classified into an intermediate or high-grade lymphoma. For the patients diagnosed with an intermediate lymphoma, the average survival period after diagnosis is 2 years to 5 years. For the patients diagnosed with a high-grade lymphoma, the average survival period after diagnosis is 6 months to 2 years. As a typical treatment for the B cell lymphoma, there may be autologous or allogenic hematopoietic stem cell transplantation, chemotherapy, and a radiation therapy. However, generally, it recurs in the coming months after being treated.

Currently, in connection with the treatment of the B cell lymphoma, the technologies, such as, a protein kinase C inhibitor (Korean Publication No. 2012-0133389), a monoclonal antibody to CD20 (Korean Publication No. 2008-0039844), the combination use of an anti-cytokine antibody and anti-CD20 (Korean Publication No. 2002-0091170), and the like, are developed, but there are no distinct treatment effects that are qualified.

Meanwhile, interleukin-21 (IL-21) amplifies the immune reactions of most lymphocyte subsets, such as, dendritic cells and monocytes, which are mainly produced in an activated CD4+ T lymphocyte and natural killer T cell. Specifically, the IL-21 promotes the proliferation and differentiation of the natural killer cell and CD8+ T lymphocyte. Therefore, there is a connection between the IL-21 and an anti-tumor immune response. However, the systemic administration of a recombinant IL-21 protein, a IL-21 expressing plasmid DNA, or a IL-21 expressing virus, which is known as a treatment using IL-21, has a limited ability for the movement into a tumor lesion, and thus, does not exhibit strong anti-tumor effectiveness.

Therefore, the development of the drugs, which can effectively deliver IL-21 toward a tumor lesion, and thus, can consistently express an anti-tumor effectiveness of IL-21 for a long period of time with high biological safety, is required.

SUMMARY OF THE INVENTION

An object of the present invention is to provide a pharmaceutical use of an IL-21 expressing mesenchymal stem cell for preventing or treating B-cell lymphoma.

In order to achieve the object, the present invention provides a pharmaceutical composition comprising IL-21 expressing mesenchymal stem cells for preventing or treating B-cell lymphoma.

The present invention also provides a use of an IL-21 expressing mesenchymal stem cell for preparing a pharmaceutical composition for preventing or treating B-cell lymphoma.

The present invention also provides a method for treating B-cell lymphoma in a subject in need thereof, in which comprises administering to said subject a pharmaceutically effective amount of a pharmaceutical composition comprising IL-21 expressing mesenchymal stem cells for preventing or treating B-cell lymphoma.

The present invention also provides a method for preparing a pharmaceutical composition for preventing or treating B-cell lymphoma, in which the method including introducing an IL-21 expressing IL-21 into a mesenchymal stem cell.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 1 illustrates the result (A) of analyzing the mesenchymal stem cells, which are infected with an IL-21 and GFP expressing adenovirus, with a fluorescence microscope and a flow cytometry apparatus (FACS), and the result of confirming and quantifying the expression amounts of IL-21 through a PCR (B) and a sandwich ELISA (C);

FIG. 2 illustrates an apoptotic effect (A) and anti-tumor cytokine secretion ability (B) of IL-21 expressing mesenchymal stem cells in the B-cell lymphoma cells, in which the results are in the group that is treated with an IL-21 expressing adenovirus (rAd/IL-21) and the group that is treated with the mesenchymal stem cells infected with an IL-21 expressing adenovirus (IL-21 MSC);

FIG. 3 illustrates a disease-free survival (A) as time passed (the number of days) in each of the control group and experimental groups) after inducing B-cell lymphoma in the experimental animals (the overall survival when the mice died, actually), and the result (B) of confirming whether or not A20 lymphoma metastasizes into spleen and liver, in which the results are in a non-treated control group (Control), a group treated with an IL-21 expressing adenovirus (rAd/IL-21), a group treated with mesenchymal stem cells (MSC), and a group treated with mesenchymal stem cells infected with an IL-21 expressing adenovirus;

FIG. 4 illustrates the results of detecting the expressions of IL-21 produced in a liver (A: ELISA) and a spleen (B: RT-PCR) that are main tumor elesions after administering euthanasia the animals of each of the control group and experimental groups at 41 days after inducing B-cell lymphoma in the experimental animals, in which the results are in a non-treated control group (Control), a group treated with mesenchymal stem cells, a group treated with an IL-21 expressing adenovirus (rAd/IL-21), and a group treated with mesenchymal stem cells infected with an IL-21 expressing adenovirus (IL-21/MSC);

FIG. 5 illustrates the results of measuring the content of cytokine secreted in the cells, and the numbers of NK cells and myeloid-derived suppressor cell (MDSC) after isolating a single cell from the spleen obtained after administering euthanasia the animals in each of the control group and experimental groups at 41 days after inducing B-cell lymphoma in the experimental animals, in which the results are in a non-treated control group (Control), a group treated with mesenchymal stem cells, a group treated with an IL-21 expressing adenovirus (rAd/IL-21), and a group treated with mesenchymal stem cells infected with an IL-21 expressing adenovirus (IL-21 MSC); and FIG. 6 illustrates the apoptotic effect of an IL-21 expressing mesenchymal stem cell, which is specific to B-cell lymphoma.

DETAILED DESCRIPTION OF EXEMPLARY EMBODIMENTS

Hereinafter, the present invention will be described with reference to examples and comparative examples in detail. However, the present invention is not limited to these examples.

The present inventors prepared mesenchymal stem cells that over-express IL-21 by introducing IL-21 into mesenchymal stem cells (FIG. 1). The supernatant of IL-21 over-expressing mesenchymal stem cells is treated into B-cell lymphoma cells. As a result, there was an excellent apoptotic effect as compared with the case of treating a recombinant IL-21 protein, and especially, the expressions of TNF-α and IFN-α increased 10 times or more and 30 times or more, respectively, as compared with the group treated with mesenchymal stem cells. As a result, it could be confirmed that the IL-21 over-expressing mesenchymal stem cells exhibit IL-21 delivery ability and also a direct anti-tumor effect (FIG. 2). In addition, as a result of treating the mouse with systemically spread B-cell lymphoma by administering IL-21 expressing mesenchymal stem cells into the mouse, it can be confirmed that the survival rate thereof is improved as compared with the treatment using an IL-21 virus that is conventionally known (FIG. 3A). Furthermore, in the case of a non-treated control group, A20 lymphoma has been metastasized to liver and spleen. Therefore, it could be confirmed that the IL-21 expressing mesenchymal stem cells could prevent the metastasis in the liver (FIG. 3B). In addition, it was confirmed from the improved survival rate that the IL-21 expressing mesenchymal cells could effectively deliver IL-21 into a liver and spleen that were main tumor lesions, as compared with an IL-21 expressing virus (FIG. 4). In addition, from the result of analyzing immune cells in the isolated spleen, the improvement of immune cells was not observed in the groups only treated with IL-21 and mesenchymal stem cells, as compared with the control group. However, in the group treated with the IL-21 expressing mesenchymal stem cells, the NK cells having an anti-tumor effect, and CD8 and CD4 T cells that secret IFN-γ was increased and the number of myeloid-derived suppressor cells was significantly reduced. As a result, it could be confirmed that the IL-21 over-expressing mesenchymal stem cells could induce the strong anti-tumor immune response and also control the immune suppressor cells to directly improve the micro environment of the tumor (FIG. 5). Finally, as a result of confirming the apoptotic effect of IL-21 over-expressing mesenchymal stem cells in various tumor cell lines, it was confirmed that there were a strong apoptotic effect to B-cell lymphoma, and a weak apoptotic effect to ovarian cancer and CML (chronic myelocyte leukemia) cells, but there was no an apoptotic effect to other lymphatic system tumor cells other than B cells (FIG. 6).

Therefore, the present invention developed a novel tumor treatment based on cells by introducing IL-21 into mesenchymal stem cells based on the above-described results.

In an aspect, there is provided a pharmaceutical composition including IL-21 expressing mesenchymal stem cells for preventing or treating B-cell lymphoma.

In another aspect, there is provided a use of an IL-21 expressing mesenchymal stem cell for preparing a pharmaceutical composition for preventing or treating B-cell lymphoma.

In another aspect, there is provided a method for treating B-cell lymphoma in a subject in need thereof, in which comprises administering to said subject a pharmaceutically effective amount of a pharmaceutical composition comprising IL-21 expressing mesenchymal stem cells for preventing or treating B-cell lymphoma.

In another aspect, there is provided a method for preparing a pharmaceutical composition for preventing or treating B-cell lymphoma, in which the method includes introducing an IL-21 expressing vector into a mesenchymal stem cell.

Hereinafter, the present invention will be described in more detail.

It is reported that a mesenchymal stem cell (MSC) is a kind of an adult stem cell, does not have the carcinogenesis and ethical problems that are generally a problem in an embryonic stem cell, and also, can be differentiated into various cells, such as, a adipose cell, osteoblast, chondrocyte, cardiac cell, muscular cell, and nerve cell.

In the present invention, the mesenchymal stem cells may be isolated from bone marrow, and the like. In addition, the mesenchymal stem cells may be taken from a patient or may be isolated from the bone marrow having a matched type of HLA (human leukocyte antigen) using the database of a blood bank. Therefore, it is possible to minimize immune rejection among the individual.

According to the present invention, by introducing IL-21 gene exhibiting an anti-tumor effect into the mesenchymal stem cells, delivering the IL-21 toward a tumor lesion, and then, expressing the IL-21 in a relevant region, it is possible to solve the problems, such as the decrease in a half-life and the decrease in biological activity due to the in vivo degradation of a conventional protein medicine or virus-mediated medicine; it is possible to solve the problems of delivery efficiency and stability of a conventional gene medicine; and also it is possible to supply a continuous and stable treatment effect.

In the present invention, the IL-21 expressing mesenchymal stem cells may be obtained based on the knowledge in a prior art as an autologous or allogenic mesenchymal stem cell. For example, the IL-21 expressing mesenchymal stem cell may be obtained by proliferating or differentiating the isolated mesenchymal stem cells that are introduced with an IL-21 gene in vitro under a proper condition, or may be obtained by introducing the IL-21 gene into the mesenchymal stem cells that are sufficiently proliferated.

As an embodiment, the IL-21 expressing mesenchymal stem cells may be the mesenchymal stem cells introduced with an IL-21 expressing vector.

For the present invention, the "vector" refers to a gene constructs including a foreign DNA inserted into a genome encoding polypeptide.

The vector is a vector prepared by inserting the nucleic acid sequence of an IL-21 gene into a genome, and examples of the vectors may include a DNA vector, a plasmid vector, a cosmid vector, a bacteriophage vector, a yeast vector, or a virus vector. The appropriate expressing vector may include a leader sequence or a signal sequence for a membrane targeting or secreting in addition to an expression controlling element, such as, promoter, operator, start codon, stop codon, polyadenylation signal, and enhancer, and may be variously prepared according to the purposes. The promoter of the vector may be constitutive or inductive. In addition, the expressing vector may include a selection marker for selecting a host cell including a vector, and may include a replication origin in the case of a replicable expressing vector. Examples of the virus vector may include an adenovirus, a retrovirus, an adeno-associated virus, a herpes simplex virus, SV40, a polyomavirus, a papillomavirus, a picornavirus, a baciniavirus, or a helper dependent adenovirus, as a mediator that expresses IL-21. The viruses may be a recombinant virus. In the specific embodiment of the present invention, the IL-21 expressing adenovirus may be introduced by mesenchymal stem cells, and then may be used.

The IL-21 gene that is introduced into the vector may be a nucleic acid sequence encoding an IL-21 protein or a derivative having the characteristics that are functionally similar as the same. The nucleic acid may be DNA or RNA. In the present specification, the "derivative having the characteristics that are functionally similar" has the characteristics that are functionally similar as the IL-21, and in detail, means the derivative, in which the partial amino acid residue in a peptide is substituted, deleted, or added, and means the derivative modified with an amino group or a carboxyl group of the derivative, in which the amino acid residue in the peptide or a part of the peptide is substituted, deleted, or added.

In the present invention, a method of introducing an IL-21 expressing vector into a mesenchymal stem cell may be a known transduction method or known transfection method, and examples thereof may include a centrifuge method, a microinjection method, a calcium phosphate precipitation method, an electroporation method, a liposome-mediation transfection method, a DEAE-dextran method, and a gene bombardment method, but the present invention is not limited thereto.

The composition of the present invention exhibits an effect of preventing or treating B-cell lymphoma. The B-cell lymphoma includes various B-cell lymphomas, such as, low/follicular non-Hodgkin's lymphoma (NHL), small lymphocytic (SL) NHL, intermediate/follicular NHL, intermediate diffuse NHL, high immunoblast NHL, high lymphoblast NHL, high small non-division cell NHL, bulky disease NHL, and Waldenstrom microglobulinemia.

In the present invention, "treatment" means all kinds of actions for inhibiting, relieving, or beneficially changing a clinical situation related to a disease. In addition, the treatment may mean the increased survival rate as compared with the survival rate to be expected in the case of being non-treated. The treatment includes a preventive way in addition to a therapeutic way at the same time.

In the present invention, a "subject" may be vertebrate, preferably, a mammal, for example, a dog, a cat, a mouse, human, and the like.

The composition of the present invention may be formulated by further including a pharmaceutically acceptable carrier. In the present invention, the term, "pharmaceutically acceptable carrier" refers to a carrier or diluents that do not stimulate an organism and do not hinder the biological activities and characteristics of the administered components. In the present invention, the pharmaceutically acceptable carrier may be saline solution, sterile water, Ringer's solution, phosphate buffered saline, dextrose solution, maltodextrin solution, glycerol, ethanol, and in combination of one component or one or more components thereof. The pharmaceutically acceptable carrier may be formulated in a type of an injection that is properly injected into an internal organ or tissue by adding other general additive, such as, antioxidant, buffer, and bacteriostatic agent, if necessary. In addition, it may be also formulated in a dry formulation (especially, a freeze-dried formulation) that may be an injectable solution by adding isotonic sterile solution, or in some cases, sterile water or physiological saline.

In addition, preferably, the composition of the present invention may further include filler, excipient, a disintegrating agent, a binding agent, and a lubricant. In addition, the composition of the present invention may be formulated using the method that is known in a prior art so as to provide immediate release, extended release, or delayed release of an active component that is administered into a mammal.

In the present invention, the term, "administration" means the introduction of the composition of the present invention into a patient using a proper method, and the administering route of the composition of the present invention may be performed through various oral or parenteral routes as long as the composition may be arrived to a desired tissue. The composition of the present invention may be administered through an intraperitoneal administration, an intravenous administration, an intramuscular administration, a subcutaneous administration, an intracutaneous administration, an oral administration, a local administration, a intranasal administration, a intralung administration, and an intrarectal administration, but the present invention is not limited thereto.

In the present specification, an "effective amount" means the amount that is required to delay or completely stop the development or progress of a specific disease that should be treated. In the present invention, the composition may be administered in a pharmaceutically effective amount. It is considered by a person who skilled in the art that the proper used amount for a day may be determined by a doctor within the right medical decision range. In terms of the purpose of the present invention, it is preferable that a specific therapeutic effective amount to a specific patient depends on various factors and similarity factors that are well known in a medical field, for example, a specific composition, an age, weight, general health condition, sex, and dietary of a patient, an administration time, an administration route, and a secretion rate of a composition, a treatment period, and a drug that is used with the specific composition or is used along with the specific composition at the same time, such as, a type and a degree of a reaction, and in some cases, whether or not other formulations are used.

Hereinafter, the present invention will be described in detail with reference to Examples. However, the following Examples are only for illustrating the present invention, and the present invention is not limited to the following Examples.

EXAMPLES

<Example 1> Preparation of IL-21 Expressing Mesenchymal Stem Cells and Measurement of IL-21 Cytokine $5 \times 10^5$ cells of mesenchymal stem cells isolated from the bone marrow of Balb/c mice was treated with 8 μg/mL of polybrene and $5 \times 10^7$ pfu (100 MOI) of mIL-21 (mouse IL-21) expressing adenovirus (rAD/mIL-21) in a serum-free medium, and was infected by centrifuging the medium at 1500 rpm for 30 minutes. After 24 hours, the supernatant including the virus was removed, and then, a fresh media was further added thereto. At 3 day from the virus infection day, the cells were collected, and then, a green fluorescent protein (GFP) that was expressed along with IL-21 was measured with a flow cytometer. The production of IL-21 in the cell culture solution was estimated using a sandwich ELISA.

In order to confirm the introduction of an IL-21 gene, TriZol was treated to the IL-21 expressing mesenchymal stem cells, and then, RNA was extracted therefrom. 2 μg of the extracted RNA was quantified, and then, was reacted with an oligo dT primer, a dNTP mix, and a reverse transcriptase to synthesize cDNA. With the synthesized cDNA, a real-time quantitative PCR was performed to an IL-21-gene and β-actin, a housekeeping gene to measure the initial amount of the gene for each of the cells.

In order to confirm the secretion of IL-21 cytokine, the cells were reacted with a monoclonal anti-IL-21 antibody at 4° C. overnight in a 96 well plate, and then, after the reaction, a non-specific binding was blocked with a blocking solution (1% BSA/PBST). An IL-21 recombinant was continuously diluted by ½, and then, was used as a standard. The cell culture supernatant was added thereto, and then, was reacted at room temperature for 2 hours. Since then, it was reacted with a biotinylated anti-IL-21 antibody at room temperature for 2 hours. After the reaction, it was washed four times, and then, the diluted ExtraAvidin-Alkaline Phosphatase conjugate was added and then, was reacted at room temperature for 2 hours. After the reaction, a PNPP/DEA solution was added to be color-developed. After the color-development, the absorbance thereof was measured at a wavelength of 405 nm.

It was difficult to perform the transduction of a gene into the mesenchymal stem cells through a virus as compared with other cells. However, when the virus and polybrene were together treated thereto and the transduction was performed with a spin centrifugation method, the expression of the green fluorescence protein that was expressed along with IL-21 was confirmed through a flow cytometer (FIG. 1A), and also, it was confirmed from a PCR (FIG. 1B) and an ELISA (FIG. 1C) that the expression of the IL-21 gene and the IL-21 protein that was actually secreted were significantly increased.

<Example 2> Cytokine Secretion Comparison Between IL-21 Expressing Mesenchymal Stem Cells and General Mesenchymal Stem Cells, and In Vitro Tumor Cells-Apoptotic Effect Test Thereof After collecting IL-21 expressing mesenchymal stem cells and general mesenchymal stem cells, TriZol was treated thereto, and then, the RNA was extracted therefrom. 2 μg of the extracted RNA was quantified, and then, was reacted with an oligo dT primer, a dNTP mix, and a reverse transcriptase to synthesize cDNA. With the synthesized cDNA, a real-time quantitative PCR was performed to a target cytokine and β-actin, a housekeeping gene to measure the initial amount of the gene for each of the cells. In order to confirm a tumor cells-apoptotic effect in vitro, a recombinant IL-21 protein (500 ng/mL), the supernatant of general mesenchymal stem cells, or the supernatant of IL-21 expressing mesenchymal stem cells was treated to B-cell lymphoma A20 cells, and then, was reacted for 96 hours. A CCK-8 reagent including WST-8, water-soluble formazan dye was treated thereto. After being reacted for 3 hours, the absorbance thereof was measured at a wavelength of 450 nm.

As shown in FIG. 2, when the supernatants of MSC and IL-21/MSC were treated to B-cell lymphoma A20 cells, an apoptotic effect was excellent as compared with that of a recombinant IL-21 protein (rIL-21). It was expected that a small amount of TNF-α, IFN-α, IFN-β, or IFN-γ, that was an anti-tumor cytokine, was secreted in general MSC, and these cytokines exhibited an apoptosis effect. In addition, as compared with the general MSC, the anti-tumor cytokines were increased in IL-21 expressing MSC. Especially, the expressions of TNF-α and IFN-α were increased by 10 times or more and 30 times or more, respectively, and were linked to an apoptosis effect. Therefore, the IL-21 expressing MSC exhibited IL-21 delivery ability and also direct anti-tumor effect.

<Example 3> Induction of B-Cell Lymphoma and Treatment Effect Test Using IL-21 Expressing Mesenchymal Stem Cells A tumor model was induced by intravenously-injecting $1 \times 10^6$ cells of syngeneic A20 cells into an 8-week Balb/c mouse. At one week after injecting the tumor cells, $1 \times 10^5$ cells of IL-21 expressing mesenchymal stem cells, which were 1/10 of the tumor cells, was intravenously-injected, and then, the treatment was performed four times every one week. A normal mouse group without B-cell lymphoma, a non-treated control group, the group administered with $2 \times 10^7$ p.f.u (plaque forming unit) of IL-21 expressing adenovirus (rAD/IL-21), and the group administered with $1 \times 10^5$ cells of mesenchymal stem cells were used as a comparison group.

TABLE 1

| Control group/ experimental group | Description |
| --- | --- |
| Normal | Normal animal without B-cell lymphoma |
| Control | Non-treated control group |
| rAd/IL-21 | Group administered with IL-21 expressing adenovirus |
| MSC | Group administered with mesenchymal stem cells |
| IL-21/MSC | Group administered with mesenchymal stem cells infected with IL-21 expressing adenovirus |

A lymphoma-bearing mouse model was induced by intravenous injection of $1 \times 10^6$ cells of syngeneic A20 cells into an 8-week Balb/c mouse, and then, the IL-21 expressing mesenchymal stem cells were injected intravenously into the mouse model to confirm the therapeutic effect.

As shown in FIG. 3, when the B-cell lymphoma cells were injected intravenously, the cells were spread into a whole system. Therefore, the disease-free survival of the non-treated control group was 27 days, and when the groups were treated with rAd/IL-21 or MSC, the disease-free survival was improved by about one week as compared with the control group. The incidence rate of the B-cell lymphoma in the mice administered with IL-21/MSC was delayed, and also, 30% of the mice did not exhibit a tumor for 80 days, thereby significantly improving the diseases-free survival (FIG. 3A). In addition, in the non-treated control group, it was confirmed that A20 lymphoma was metastasized into a spleen and liver. However, in the group administered with IL-21/MSC, it was confirmed that the tumor was metastasized into a liver was prevented as compared with other administered groups (FIG. 3B).

<Example 4> Experiment for Confirming Migratory Ability of IL-21 Expressing Mesenchymal Stem Cells Toward Liver and Spleen Tissues that are Main Tumor Lesions In the case of intravenous-injecting tumor cells, the tumor cells were metastasized into a liver. Therefore, the migratory ability of IL-21 expressing mesenchymal stem cells toward a liver and spleen tissue was confirmed by investigating the expression of IL-21 produced in a liver and spleen tissue. In this regard, the tumor cells were injected; at 41 days, the Balb/c mice were euthanized; and then, the liver and spleen tissues were obtained from the dissected mice. The liver tissue was added in a buffer including 50 mM Tris-HCl, 250 mM NaCl, 5 mM EDTA, and a protease inhibitor, and then, homogenized using a homogenizer to obtain the lysate of the liver. The IL-21 in the liver of the mouse was investigated using a sandwich ELISA. In this regard, the lysate was reacted with a monoclonal anti-IL-21 antibody in a 96 well plate at 4° C. overnight, and then, after the reaction, non-specific binding was blocked with a blocking solution (1% BSA/PBST). An IL-21 recombinant was continuously diluted by ½, and then, was used as a standard. The cell culture supernatant was added thereto, and then, after adding the lysate of the liver thereto, the supernatant was reacted at room temperature for 2 hours. Since then, it was reacted with a biotinylated anti-IL-21 antibody at room temperature for 2 hours. After the reaction, it was washed four times, and then, the diluted ExtraAvidin-Alkaline Phosphatase conjugate was added and then, was reacted at room temperature for 2 hours. After the reaction, a PNPP/DEA solution was added to be color-developed. After the color-development, the absorbance thereof was measured at a wavelength of 405 nm.

The spleen cells were isolated as a single cell, and collected. TriZol was treated thereto, and then, RNA was extracted therefrom. 2 μg of the extracted RNA was quantified, and then, was reacted with an oligo dT primer, a dNTP mix, and a reverse transcriptase to synthesize cDNA. With the synthesized cDNA, a real-time quantitative PCR was performed to an IL-21 cytokine gene and β-actin, a house-keeping gene to measure the initial amount of the IL-21 gene in the spleen for each of the groups.

As shown in FIG. 4, the expression of IL-21 in the liver and spleen of the group administered with IL-21/MSC was higher than other groups. From these results, it was confirmed that IL-21/MSCs delivered IL-21 into a tumor lesion, more effectively, as compared with rAD/IL-21.

<Example 5> Experiment for Confirming Ability of IL-21 Expressing Mesenchymal Stem Cells on Improving Tumor Micro Environment The tumor cells were injected and the Balb/c mice were euthanized at 41 days, and then, the spleens were obtained from the dissected mice. After the spleen was isolated as a single cell, CD3 and CD49b that were NK cell-specific surface proteins, CD8 that was an effector T cell-specific surface protein, CD11b that was a myeloid-derived suppressor cell-specific surface protein, and a fluorescence binding antibody to Gr-1 were each added, and then, reacted. In order to measure the cytokines secreted in an effector CD8+ T cell, PMA, Ionomycin, and Golgistop were further added to a single cell of spleen, and then, the reaction was performed for 4 hours. After collecting the single cells that were secondarily stimulated, the antibodies to the surface proteins were first reacted, the cells were fixed; and then, the cells were reacted with the reagent for the permeabilization into a cell membrane. Finally, the antibody to IFN-γ was added and then reacted. The single cell thus stained could be analyzed using a flow cytometer.

As shown in FIG. 5, the immune cells in the groups, which were administered with MSC and IL-21, separately, were not significantly improved as compared with the control group. However, in the group administered with IL-21/MSC, the NK cells, a main immune cell, and CD8 and CD4 T cells that secreted anti-tumor cytokines, which had an anti-tumor effect, were increased as compared with the control group and other groups. In addition, the myeloid-derived suppressor cell (MDSC) that was an immunosuppressive cell was significantly decreased in the group administered with IL-21/MSC. Therefore, it was confirmed that the IL-21/MSC induces a strong anti-tumor immune response in vivo, and also, controls an immunosuppressive cell so as to directly improve a tumor micro environment.

<Example 6> Experiment for Confirming B-Cell Lymphoma-Specific Apoptotic Effect of IL-21 Expressing Mesenchymal Stem Cells In order to confirm an apoptotic effect to human tumor cell lines, the IL-21/MSC of human was prepared in the same method as the IL-21/MSC of mouse. In order to confirm a tumor cell-apoptotic effect in vitro, the supernatant of human IL-21 expressing mesenchymal stem cells was treated to human B-cell lymphoma cell Jiyoye, ovarian carcinoma cell SK-OV3, NK/T cell lymphoma cell Hank-1, NK cell lymphoma cell NK-92, and chronic myeloid leukemia cell K562, and then, reacted for 96 hours. A CCK-8 reagent including WST-8, water-soluble formazan dye, was further added thereto. After being reacted for 3 hours, the absorbent thereof was measured at a wavelength of 450 nm.

As shown in FIG. 6, when the supernatant of IL-21/MSC was treated to various tumor cell lines, the supernatant of IL-21/MSC exhibited a strong apoptotic effect on B-cell lymphoma. The supernatant of IL-21/MSC exhibited an apoptotic effect on an ovarian cancer and chronic myeloid leukemia cell, but the apoptotic effect on B-cell lymphoma was stronger. In addition, the supernatant of IL-21/MSC did not exhibit the apoptotic effect on other lymphatic tumor cells other than B cell.

The present invention can provide a novel tumor therapeutic method based on cells, in which the method can effectively deliver IL-21 into a tumor lesion, can continuously express an anti-tumor effect of IL-21 for a long period of time, and has high biological safety.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A method for treating B-cell lymphoma comprising,
   administering mesenchymal stem cells (MSCs) derived from bone marrow in an amount effective to treat the B-cell lymphoma to a vertebrate subject having B-cell lymphoma,
   wherein the MSCs express IL-21 and have an increased expression of an antitumor cytokine selected from the group consisting of TNF-α and IFN-α as compared to a naïve MSC,
   wherein the increased expression of the antitumor cytokine TNF-α and IFN-α in the IL-21 expression MSCs is at least ten times and at least thirty times respectively that of a naïve MSC, and
   wherein the vertebrate subject is a non-human vertebrate subject.

2. The method of claim 1, wherein the mesenchymal stem cells are a mesenchymal stem cell introduced with an IL-21 expressing vector.

3. The method of claim 2, wherein the vector is a virus vector.

4. The method of claim 3, wherein the virus vector is a recombinant adenovirus.

5. The method of claim 1, wherein the non-human vertebrate subject is a dog, a cat, or a mouse.

\* \* \* \* \*